(12) United States Patent
Xu et al.

(10) Patent No.: US 9,844,770 B2
(45) Date of Patent: Dec. 19, 2017

(54) CATALYST USED IN THE PRODUCTION OF ETHYLENE AND PROPYLENE FROM METHANOL AND/OR DIMETHYL ETHER, METHOD FOR PREPARING THE SAME AND METHOD FOR USING THE SAME

(75) Inventors: Lei Xu, Dalian (CN); Zhongmin Liu, Dalian (CN); Shukui Zhu, Dalian (CN); Zhengxi Yu, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 206 days.

(21) Appl. No.: 14/366,156

(22) PCT Filed: Apr. 23, 2012

(86) PCT No.: PCT/CN2012/074518
§ 371 (c)(1),
(2), (4) Date: Jun. 17, 2014

(87) PCT Pub. No.: WO2013/091335
PCT Pub. Date: Jun. 27, 2013

(65) Prior Publication Data
US 2015/0005559 A1    Jan. 1, 2015

(30) Foreign Application Priority Data
Dec. 19, 2011   (CN) .......................... 2011 1 0427280

(51) Int. Cl.
| C07C 1/22 | (2006.01) |
| B01J 29/40 | (2006.01) |
| C07C 1/20 | (2006.01) |

(52) U.S. Cl.
CPC ............. *B01J 29/405* (2013.01); *C07C 1/20* (2013.01); *C07C 1/22* (2013.01); *B01J 2229/186* (2013.01); *B01J 2229/32* (2013.01); *C07C 2523/10* (2013.01); *C07C 2529/06* (2013.01); *C07C 2529/40* (2013.01); *Y02P 20/52* (2015.11); *Y02P 30/42* (2015.11)

(58) Field of Classification Search
CPC .. C07C 1/20; C07C 1/22; C07C 11/04; C07C 11/06; B01J 29/405
See application file for complete search history.

(56) References Cited

U.S. PATENT DOCUMENTS

| 3,911,041 A | 10/1975 | Kaeding et al. |
| 4,035,430 A | 7/1977 | Dwyer et al. |
| 4,049,573 A | 9/1977 | Kaeding |
| 4,100,219 A | 7/1978 | Rodewald |
| 4,440,871 A | 4/1984 | Lok et al. |
| 4,499,314 A * | 2/1985 | Seddon ..................... C07C 1/20 585/357 |
| 4,542,252 A | 9/1985 | Graziani et al. |
| 5,367,100 A | 11/1994 | Gongwei et al. |
| 6,046,372 A * | 4/2000 | Brown ................... B01J 29/005 585/639 |

FOREIGN PATENT DOCUMENTS

| CN | 1431982 A | | 7/2003 |
| CN | 101417235 A | * | 4/2009 |
| CN | 101767038 A | * | 7/2010 |
| CN | 101780417 A | * | 7/2010 |
| EP | 0006501 A1 | | 1/1980 |
| JP | 60-126233 A | | 7/1985 |
| JP | 61-97231 A | | 5/1986 |
| JP | 62-70324 A | | 3/1987 |
| JP | 2009255014 A | | 11/2009 |

OTHER PUBLICATIONS

Translation of CN101417235 A.*
CN 101417235 A Translation.*

* cited by examiner

*Primary Examiner* — Brian McCaig
*Assistant Examiner* — Jason Chong
(74) *Attorney, Agent, or Firm* — Nath, Goldberg & Meyer; Tanya E. Harkins; Joshua B. Goldberg

(57) ABSTRACT

The application provides a catalyst for producing ethylene and propylene from methanol and/or dimethyl ether, and a preparation and application thereof. In the present application, a molecular sieve catalyst co-modified by rare earth metals and silanization is utilized. First, the material containing methanol and/or dimethyl ether reacts on the catalyst to generate hydrocarbons. The hydrocarbons are separated into a $C_1$-$C_5$ component and a $C_6^+$ component. Then the $C_6^+$ component is recycled to the feeding port and fed into the reactor after mixing with methanol and/or dimethyl ether. The above steps are repeated, to finally generate $C_1$-$C_5$ products, in which the selectivity for ethylene and propylene can reach more than 90 wt % in the $C_1$-$C_5$ component, so that the maximal yield can be achieved in the production of ethylene and propylene from methanol and/or dimethyl ether.

6 Claims, No Drawings

CATALYST USED IN THE PRODUCTION OF ETHYLENE AND PROPYLENE FROM METHANOL AND/OR DIMETHYL ETHER, METHOD FOR PREPARING THE SAME AND METHOD FOR USING THE SAME

This is a National Phase Application filed under 35 U.S.C. 371 as a national stage of PCT/CN2012/074518, filed Apr. 23, 2012, and claims priority benefit from Chinese Application No. 201110427280.0, filed Dec. 19, 2011, the content of each of which is hereby incorporated by reference in its entirety.

TECHNICAL FIELD

The present disclosure relates to a technical field of producing low-carbon alkenes from methanol and/or dimethyl ether. More specifically, the present disclosure relates to a catalyst used in the production of ethylene and propylene from methanol and/or dimethyl ether. Further, the present disclosure relates to a method for preparing said catalyst. Still further, the present disclosure relates to a highly selective process of producing ethylene and propylene from methanol and/or dimethyl ether using said catalyst and material circulation technology.

BACKGROUND

Ethylene and propylene are the essential materials used in modern chemical engineering. In chemical industry, ethylene and propylene, as mainly originated from light oils (naphtha and light diesel) through processing of petroleum, fully rely on petroleum resources. Along with the economic development, more-and-more alkenes are required. Therefore, developing a new technology for alkene production has always been an important research direction. Thereinto, the methanol to olefins process has been regarded as the most successful non-petrochemical route for producing ethylene and propylene from coal resource. For the past decades, a huge amount of both human and material resources have been devoted to the research of the process.

In 1976, the Mobil Oil Corporation, for the first time conducted conversion reaction of methanol into hydrocarbons on a ZSM-5 molecular sieve catalyst. After that, the conversion from methanol to gasoline on a ZSM-5 molecular sieve catalyst was disclosed in U.S. Pat. No. 4,035,430; the technology of producing low-carbon alkenes from methanol on a ZSM-5 molecular sieve catalyst was disclosed in U.S. Pat. No. 4,542,252; and the process for producing low-carbon alkenes from methanol on a ZSM-5 molecular sieve catalyst modified by phosphorus, magnesium, silicon or alkali metal elements was disclosed in U.S. Pat. No. 3,911,041, U.S. Pat. No. 4,049,573, U.S. Pat. No. 4,100,219, JP 60-126233, JP 61-97231, JP 62-70324 and EP 6501.

Additionally, the applicant also disclosed the reaction for producing low-carbon alkenes from methanol or dimethyl ether using a ZSM-5 molecular sieve catalyst modified by phosphorus and lanthanum in U.S. Pat. No. 5,367,100. Following this reaction, the total selectivity for ethylene and propylene was only about 65 wt % and the total selectivity for ethylene, propylene and butylenes was more than 85 wt % in the gas-phase product.

In 1984, a series of novel silicoaluminophosphate molecular sieves (SAPO-n) were developed in the Union Carbide Corporation (UCC) (U.S. Pat. No. 4,440,871). Thereinto, SAPO-34 molecular sieve exhibited an excellent catalytic performance in MTO reaction because of its proper acidity and pore structure. Replacing the ZSM-5 zeolite molecular sieve, it became the active component in the new generation of MTO catalysts. Because the pores in SAPO-34 have smaller sizes and elliptical cage structure, and coking deactivation occurs easily in methanol conversion, the MTO catalyst which utilizes SAPO-34 molecular sieve as its active component needs to be made into a microspherical fluidized catalyst and is applied to fluidization reaction process. Loss of catalysts cannot be avoided in a fluidization reaction, due to the frequent regeneration and abrasion of catalysts. As a result, the production cost of the MTO process is increased.

In order to overcome the shortages found in the fluidized bed technology for producing alkenes from methanol, development of anti-coking catalysts and fixed bed technology (involving less catalyst abrasion) is still an important research direction in this field. As known from the above prior art, while on the catalyst which utilizes ZSM-5 zeolite molecular sieve as its active component, one of the major reasons for causing a lower selectivity for ethylene and propylene in the products is that a great amount of arene products are generated in methanol conversion. Therefore, the routes for improving the selectivity for ethylene and propylene in the products include: (1) further converting the obtained arenes into alkenes; or (2) recycling the obtained arenes to facilitate the production of alkenes and suppress the generation of arene products.

DISCLOSURE

The objects of the invention are to provide a catalyst for producing ethylene and propylene from methanol and/or dimethyl ether; a method for producing the catalyst; and a process of producing ethylene and propylene using said catalyst, wherein the selectivity for ethylene and propylene is more than 90 wt % in the hydrocarbon products, so that the product recovery rate and raw material utilization rate can be improved in the conversion from methanol and/or dimethyl ether to ethylene and propylene.

For achieving the above objects, a molecular sieve catalyst co-modified by lanthanum and silanization was investigated and developed. Lanthanum-caused modification can sufficiently alter the acidity and hydrothermal stability of zeolite molecular sieve, and silanization modification causes a "passivation" to the acidity on the external surface of zeolite molecular sieve. The catalyst co-modified by lanthanum and silanization can, while used for producing ethylene and propylene from methanol and/or dimethyl ether, reduce the alkanes generated in the products and improve the selectivity for ethylene and propylene. In addition, the inventors also proposed a method to facilitate methanol and/or dimethyl ether to be converted into alkenes and to suppress the generation of arene products by co-feeding the obtained arenes and methanol and/or dimethyl ether using a recycling technique, so as to improve the selectivity for ethylene and propylene. The present application is accomplished based on the above concept.

Therefore, in one aspect, the invention provides a catalyst used for producing ethylene and propylene from methanol and/or dimethyl ether, i.e. a molecular sieve catalyst co-modified by lanthanum and silanization. In said molecular sieve catalyst, the molecular sieve is HZSM-5 and/or HZSM-11 zeolite molecular sieve. The catalyst is loaded by lanthanum and silicon compounds after co-modified by lanthanum and silanization. The loading amount of the lanthanum is 0.5-5 wt % of the total weight of said catalyst;

the loading amount of the silicon compounds, which is based on silicon oxide, is 0.1-10 wt % of the total weight of said catalyst; and the rest of said catalyst is HZSM-5 and/or HZSM-11 zeolite molecular sieve.

In a preferable embodiment, the loading amount of the lanthanum is 1-5 wt % of the total weight of said catalyst; the loading amount of the silicon compounds, which is based on silicon oxide, is 1-10 wt % of the total weight of said catalyst; and the rest of said catalyst is HZSM-5 and/or HZSM-11 zeolite molecular sieve.

In another aspect, the present application provides a method for producing said catalyst. The method comprising the steps as follows:

HZSM-5 and/or HZSM-11 zeolite molecular sieve is impregnated in a lanthanum nitrate solution for 1-12 hours, then filtered, dried and calcined to obtain lanthanum-modified molecular sieve; and said obtained lanthanum-modified molecular sieve is impregnated in a silicon source for 1-12 hours, then filtered, dried and calcined to obtain a molecular sieve catalyst co-modified by lanthanum and silanization.

Wherein said silicon source is one or more selected from a group consisting of tetramethyl silicate, tetraethyl silicate and silicon tetraethyl.

In a preferable embodiment, said silicon source is tetraethyl silicate.

In yet another aspect, the present application provides a process of producing ethylene and propylene from methanol and/or dimethyl ether. The process comprises the steps of:

(a) contacting methanol and/or dimethyl ether with said catalyst, to generate a first hydrocarbons;

(b) separating said first hydrocarbons obtained from step (a) into a first $C_1$-$C_5$ component and a first $C_6^+$ component, wherein the first $C_1$-$C_5$ component is separated as a byproduct;

(c) mixing said first $C_6^+$ component obtained from step (b) with methanol and/or dimethyl ether to generate a mixture material, and contacting the mixture material with said catalyst according to claim 1, then allowing the mixture material to react and generate a second hydrocarbons; wherein the $C_6^+$ component facilitates methanol and/or dimethyl ether to be highly selectively converted into ethylene and propylene, and hydrocarbons containing ethylene and propylene in a high selectivity is generated after the reaction;

(d) separating said second hydrocarbons obtained from step (c) into a second $C_1$-$C_5$ component and a second $C_6^+$ component, both components containing ethylene and propylene, wherein said second $C_1$-$C_5$ component is collected as the target product and said second $C_6^+$ component is recycled to step (c); and the second $C_1$-$C_5$ component is collected as the target product; and (e) repeating step (c) and step (d), wherein a mixture material formed by mixing said second $C_6^+$ component obtained in step (d) with methanol and/or dimethyl ether is used in step (c), wherein the $C_6^+$ component is recycled, and fed into a mixture with methanol and/or dimethyl ether to react, so that said second $C_1$-$C_5$ component containing ethylene and propylene in a high selectivity is obtained continuously.

In a preferable embodiment, the reaction is carried out at a temperature of 400-600° C. and a pressure of 0-2.0 MPa; and methanol and/or dimethyl ether are/is fed in a weight space hourly velocity of 0.2-10 h$^{-1}$.

In a preferable embodiment, the process is conducted in a fixed bed, a moving bed or a fluidized bed reactor.

DETAILED EMBODIMENTS

In order to achieve the above objects, a catalyst used for producing ethylene and propylene from methanol and/or dimethyl ether is investigated and developed, i.e. a molecular sieve catalyst co-modified by lanthanum and silanization. In said molecular sieve catalyst, the molecular sieve is HZSM-5 and/or HZSM-11 zeolite molecular sieve. Said catalyst co-modified by lanthanum and silanization is loaded by lanthanum and its surface acidity is modified by silicon compounds. The loading amount of the lanthanum is 0.5-5 wt % of the total weight of said catalyst; the loading amount of the silicon compounds, which is based on silicon oxide, is 0.1-10 wt % of the total weight of said catalyst; and the rest of said catalyst is HZSM-5 and/or HZSM-11 zeolite molecular sieve.

A method for producing said catalyst is investigated and developed, wherein said zeolite molecular sieve is HZSM-5 and HZSM-11 zeolite molecular sieve. The method comprises the steps as follows: HZSM-5 and/or HZSM-11 zeolite molecular sieve is impregnated in a lanthanum nitrate solution for 1-12 hours, then filtered, dried at 100-120° C. and calcined in air at 450-650° C. to obtain lanthanum-modified molecular sieve; and said obtained lanthanum-modified molecular sieve is impregnated in one or more silicon sources selected from a group consisting of tetramethyl silicate, tetraethyl silicate and silicon tetraethyl, preferably tetraethyl silicate, for 1-12 hours, then filtered, dried at 100-120° C. and calcined in air at 450-650° C. to obtain a molecular sieve catalyst co-modified by lanthanum and silanization.

A new process for producing ethylene and propylene from methanol and/or dimethyl is investigated and developed. The process comprises the steps of: contacting methanol and/or dimethyl ether alone with said catalyst, to generate a first hydrocarbons; separating said first hydrocarbons into a first $C_1$-$C_5$ component and a first $C_6^+$ component; recycling said first $C_6^+$ component and allowing it to be fed in a mixture with methanol and/or dimethyl ether; contacting the mixture with said catalyst to generate a second hydrocarbons having a new composition; separating said second hydrocarbons having the new composition into a second $C_1$-$C_5$ component and a second $C_6^+$ component; recycling said second $C_6^+$ component and collecting said second $C_1$-$C_5$ component as the product; wherein by recycling said second $C_6^+$ component and feeding it in a mixture with methanol and/or dimethyl ether, the conversion from methanol and/or dimethyl ether to ethylene and propylene is improved, so that said second $C_1$-$C_5$ product containing ethylene and propylene in a high selectivity is obtained continuously.

In said catalyst, the loading amount of the lanthanum is 0.5-5 wt %, preferably 1-5% of the total weight of said catalyst; and the loading amount of the silicon oxide modified by silanization is 0.1-10 wt %, preferably 1-10% of the total weight of said catalyst.

In the process of the present application, the raw material is methanol or dimethyl ether or a mixture of methanol and dimethyl ether. Wherein said methanol is pure methanol or an aqueous solution of methanol, and the concentration of methanol in aqueous solution is between 50 wt % and 100 wt %. After vaporized, the raw material is pumped into a reactor, then contacting with said catalyst and converting to target products.

In a preferable embodiment, said process of converting methanol/dimethyl ether into ethylene and propylene is conducted in a fixed bed, a moving bed, or a fluidized bed.

In a preferable embodiment, said process of converting methanol/dimethyl ether into ethylene and propylene is carried out at temperature of 350-650° C., more preferably 400-600° C.; and a pressure of 0-5.0 MPa, more preferably 0-2.0 MPa; and the raw material is fed in a weight space hourly velocity of 0.2-10 h$^{-1}$, more preferably 0.2-10 h$^{-1}$.

In present application, said pressure is a gage pressure.

For the catalyst used in the conversion from methanol/dimethyl ether to ethylene and propylene and the application thereof according to the present application, a $C_1$-$C_5$ product containing ethylene and propylene in a high selectivity is obtained finally, wherein the selectivity for ethylene and propylene is more than 90 wt % in the $C_1$-$C_5$ product.

EXAMPLES

The application is described in detail by the following Examples, but not limited to the Examples.

In this application, the parts, percentages and amounts are all based on weight, unless indicated otherwise.

Example 1: Preparation of Catalyst

1) The raw powder containing a template agent inside of HZSM-5 zeolite molecular sieve (100 g, The Catalyst Plant of Nankai University, molar ratio of $SiO_2/Al_2O_3$=50) was weighted, and then impregnated overnight in a lanthanum nitrate solution which was prepared according to the requirement of 3 wt % La loading amount. After the upper layer liquid was decanted, the impregnated HZSM-5 zeolite molecular sieve solid was dried out at 120° C., and calcined in air at 550° C. for 3 hours. Then La-modified HZSM-5 zeolite molecular sieve was obtained.

2) The La-modified HZSM-5 zeolite molecular sieve (50 g) obtained in step (a) was impregnated in tetraethoxysilane (TEOS) at room temperature for 12 hours. After the upper layer liquid was decanted, the impregnated HZSM-5 zeolite molecular sieve solid was dried out at 120° C., and calcined in air at 550° C. for 6 hours. Then a HZSM-5 catalyst co-modified by lanthanum and silanization was obtained, and named as MATO-1.

3) The HZSM-5 catalyst co-modified by lanthanum and silanization was subjected to an elemental analysis, wherein the loading amount of lanthanum was 2.8 wt % of the total weight of said catalyst and the loading amount of silanization, which was based on silicon oxide, was 4.8% of the total weight of said catalyst.

Example 2: Preparation of Catalyst

1) The raw powder containing a template agent inside of HZSM-5 zeolite molecular sieve (100 g, The Catalyst Plant of Nankai University, molar ratio of $SiO_2/Al_2O_3$=50) was weighted, and then impregnated overnight in a lanthanum nitrate solution which was prepared according to the requirement of 5 wt % La loading amount. After the upper layer liquid was decanted, the impregnated HZSM-5 zeolite molecular sieve solid was dried out at 120° C., and baked in air at 550° C. for 3 hours. Then La-modified HZSM-5 zeolite molecular sieve was obtained.

2) The La-modified HZSM-5 zeolite molecular sieve (50 g) obtained in step (a) was impregnated in tetraethoxysilane (TEOS) at room temperature for 24 hours. After the upper layer liquid was decanted, the impregnated HZSM-5 zeolite molecular sieve solid was dried out at 120° C., and calcined in air at 550° C. for 6 hours. Then a HZSM-5 catalyst co-modified by lanthanum and silanization was obtained, and named as MATO-2.

3) The HZSM-5 catalyst co-modified by lanthanum and silanization was subjected to an elemental analysis, wherein the loading amount of lanthanum was 4.6 wt % of the total weight of said catalyst and the loading amount of silanization, which was based on silicon oxide, was 6.9% of the total weight of said catalyst.

Example 3: Preparation of Catalyst

1) The raw powder containing a template agent inside of HZSM-11 zeolite molecular sieve (100 g, The Catalyst Plant of Nankai University, molar ratio of $SiO_2/Al_2O_3$=61) was weighted, and then impregnated overnight in a lanthanum nitrate solution which was prepared according to the requirement of 5 wt % La loading amount. After the upper layer liquid was poured off, the impregnated HZSM-11 zeolite molecular sieve solid was dried out at 120° C., and calcined in air at 550° C. for 3 hours. Then La-modified HZSM-11 zeolite molecular sieve was obtained.

2) The La-modified HZSM-11 zeolite molecular sieve (50 g) obtained in step (a) was impregnated in tetraethoxysilane (TEOS) at room temperature for 24 hour. After the upper layer liquid was poured off, the impregnated HZSM-11 zeolite molecular sieve solid was dried out at 120° C., and calcined in air at 550° C. for 6 hours. Then a HZSM-11 catalyst co-modified by lanthanum and silanization was obtained, and named as MATO-3.

3) The HZSM-11 catalyst co-modified by lanthanum and silanization was subjected to an elemental analysis, wherein the loading amount of lanthanum was 4.8 wt % of the total weight of said catalyst and the loading amount of silanization, which was based on silicon oxide, was 7.3% of the total weight of said catalyst.

Reference Example: Evaluation for Reactions

The MATO-1, MATO-2 and MATO-3 catalysts were used as the catalysts in the reactions. The catalysts were tabletted, crushed and then sieved to 40-60 meshes. Ten grams of each catalyst was loaded into a reactor, and treated in air at 550° C. for 1 hour followed by being blown and purged in nitrogen for 0.5 hour. Methanol was pumped into the reactor using a feeding pump, then it was contacted and reacted with the catalyst at a temperature of 550° C. and a pressure of 0 MPa. The raw material methanol was fed in a weight space hourly velocity of 2 h$^{-1}$. The reaction products were analyzed online by gas chromatography. The compositions of the total products, the $C_1$-$C_5$ component and the $C_6^+$ component were shown in Tables 1, 2 and 3. In the total products, the $C_1$-$C_5$ component accounted for 84.26 wt %, 85.63 wt % and 85.89 wt %, respectively; whereas the $C_6^+$ component accounted for 15.74 wt %, 14.37 wt % and 14.11 wt %, respectively. In the $C_1$-$C_5$ components, the selectivity for ethylene and propylene was 56.19 wt %, 53.52 wt % and 55.23 wt %, respectively.

TABLE 1

| | Catalyst | | |
| --- | --- | --- | --- |
| | MATO-1 | MATO-2 | MATO-3 |
| Reaction temperature (° C.) | 550 | 550 | 550 |
| Conversion rate of methanol (%) | 100 | 100 | 100 |
| Distribution of total products (wt %) | | | |
| $C_1$-$C_5$ | 84.26 | 85.63 | 85.89 |
| $C_6^+$ | 15.74 | 14.37 | 14.11 |
| Total | 100.00 | 100.00 | 100.00 |

* $C_6^+$ represents the hydrocarbon products with carbon number no less than six.

TABLE 2

| | Catalyst | | |
|---|---|---|---|
| | MATO-1 | MATO-2 | MATO-3 |
| Reaction temperature (° C.) | 550 | 550 | 550 |
| Conversion rate of methanol (%) | 100 | 100 | 100 |
| Distribution of $C_1$-$C_5$ products (wt %) | | | |
| $CH_4$ | 5.32 | 5.58 | 5.64 |
| $C_2H_4$ | 13.88 | 12.25 | 12.90 |
| $C_2H_6$ | 3.52 | 3.35 | 4.23 |
| $C_3H_6$ | 42.31 | 41.27 | 42.33 |
| $C_3H_8$ | 7.34 | 7.85 | 8.37 |
| $C_4$ | 17.35 | 18.16 | 17.21 |
| $C_5$ | 10.28 | 11.54 | 9.32 |
| Total | 100.00 | 100.00 | 100.00 |
| $C_2H_4 + C_3H_6$ | 56.19 | 53.52 | 55.23 |

TABLE 3

| | Catalyst | | |
|---|---|---|---|
| | MATO-1 | MATO-2 | MATO-3 |
| Reaction temperature (° C.) | 550 | 550 | 550 |
| Conversion rate of methanol (%) | 100 | 100 | 100 |
| Distribution of *$C_6^+$ products (wt %) | | | |
| Benzene | 10.23 | 9.52 | 8.96 |
| Toluene | 36.14 | 35.28 | 36.25 |
| Ethyl benzene | 1.28 | 1.05 | 1.56 |
| Xylene | 32.54 | 34.26 | 33.21 |
| Trimethyl benzene | 11.26 | 10.89 | 11.08 |
| Tetramethylbenzene | 5.34 | 5.68 | 6.01 |
| Others | 3.21 | 3.32 | 2.93 |
| Total | 100.00 | 100.00 | 100.00 |

*$C_6^+$ represents the hydrocarbon products with carbon number no less than six.

Example 4: Evaluation for Reactions

The MATO-1, MATO-2 and MATO-3 catalysts were used as the catalysts in the reactions. The catalysts were tabletted, crushed and then sieved to 40-60 meshes. Ten grams of each catalyst was loaded into a reactor, and treated in air at 550° C. for 1 hour followed by a cooling process in nitrogen to reach the reaction temperature of 450° C. Arene solutions were prepared according to requirement for the proportions of benzene, toluene, xylene, trimethyl benzene and tetramethylbenzene in the $C_6^+$ products obtained from the methanol conversion performed on MATO-2 catalyst, as shown in Table 3 of Example 3. The prepared arene solutions and methanol (calculated by $CH_2$), in a ratio of 1:1 by weight, were pumped into the reactors by a metering pump, then they were contacted and reacted with the catalysts. The reactions were carried out at a pressure of 0 MPa. Methanol was fed in a weight space hourly velocity of 1 $h^{-1}$. The reaction products were analyzed online by gas chromatography. The compositions of the total products, the $C_1$-$C_5$ component and the $C_6^+$ component are shown in Tables 4, 5 and 6. In the total products, the $C_1$-$C_5$ component accounted for 52.15 wt %, 53.24 wt % and 53.76 wt %, respectively; whereas the $C_6^+$ component accounted for 47.85 wt %, 46.76 wt % and 46.24 wt %, respectively. In the $C_1$-$C_5$ components, the selectivity for ethylene and propylene was 90.43 wt %, 90.45 wt % and 90.11 wt %, respectively.

TABLE 4

| | Catalyst | | |
|---|---|---|---|
| | MATO-1 | MATO-2 | MATO-3 |
| Reaction temperature (° C.) | 450 | 450 | 450 |
| Conversion rate of methanol (%) | 100 | 100 | 100 |
| Distribution of total products (wt %) | | | |
| $C_1$-$C_5$ | 52.15 | 53.24 | 53.76 |
| $C_6^+$ | 47.85 | 46.76 | 46.24 |
| Total | 100.00 | 100.00 | 100.00 |

* $C_6^+$ represents the hydrocarbon products with carbon number no less than six.

TABLE 5

| | Catalyst | | |
|---|---|---|---|
| | MATO-1 | MATO-2 | MATO-3 |
| Reaction temperature (° C.) | 450 | 450 | 450 |
| Conversion rate of methanol (%) | 100 | 100 | 100 |
| Distribution of $C_1$-$C_5$ products (wt %) | | | |
| $CH_4$ | 1.56 | 1.58 | 1.52 |
| $C_2H_4$ | 52.88 | 52.70 | 51.65 |
| $C_2H_6$ | 0.04 | 0.05 | 0.04 |
| $C_3H_6$ | 37.55 | 37.75 | 38.46 |
| $C_3H_8$ | 0.55 | 0.51 | 0.46 |
| $C_4$ | 6.21 | 6.13 | 6.44 |
| $C_5$ | 1.21 | 1.27 | 1.42 |
| Total | 100.00 | 100.00 | 100.00 |
| $C_2H_4 + C_3H_6$ | 90.43 | 90.45 | 90.11 |

TABLE 6

| | Catalyst | | |
|---|---|---|---|
| | MATO-1 | MATO-2 | MATO-3 |
| Reaction temperature (° C.) | 450 | 450 | 450 |
| Conversion rate of methanol (%) | 100 | 100 | 100 |
| Distribution of *$C_6^+$ products (wt %) | | | |
| Benzene | 5.11 | 5.35 | 5.16 |
| Toluene | 15.53 | 16.36 | 15.23 |
| Ethyl benzene | 1.04 | 1.13 | 1.32 |
| Xylene | 55.29 | 54.57 | 56.11 |
| Trimethyl benzene | 14.26 | 13.35 | 12.81 |
| Tetramethylbenzene | 5.34 | 5.68 | 6.01 |
| Others | 3.43 | 3.56 | 3.36 |
| Total | 100 | 100 | 100 |

*$C_6^+$ represents the hydrocarbon products with carbon number no less than six.

Example 5: Evaluation for Reactions

The MATO-1, MATO-2 and MATO-3 catalysts were used as the catalysts in the reactions. The catalysts were tabletted, crushed and then sieved to 40-60 meshes. Ten grams of each catalyst was loaded into a reactor, and treated in air at 550° C. for 1 hour followed by a cooling process in nitrogen to reach the reaction temperature of 500° C. Arene solutions were prepared according to the requirement for the proportions of benzene, toluene, xylene, trimethyl benzene and tetramethylbenzene in the $C_6^+$ products obtained from the methanol conversion performed on MATO-2 catalyst, as shown in Table 6 of Example 4. The prepared arene solutions and methanol (calculated by $CH_2$), in a ratio of 1:1 by weight, were pumped into the reactors by a metering pump, then they were contacted and reacted with the catalysts. The pressure in the reaction system was adjusted to 0.5 MPa using a back pressure valve. Methanol was fed in a weight space hourly velocity of 4 $h^{-1}$. The reaction products were analyzed online by gas chromatography. The compositions of the total products, the $C_1$-$C_5$ component and the $C_6^+$ component are shown in Tables 7, 8 and 9. In the total products, the $C_1$-$C_5$ component accounted for 50.32 wt %, 51.86 wt % and 51.21 wt %, respectively; whereas the $C_6^+$ component accounted for 49.68 wt %, 48.14 wt % and 48.79 wt %, respectively. In the $C_1$-$C_5$ components, the selectivity for ethylene and propylene was 90.95 wt %, 91.22 wt % and 91.45 wt %, respectively.

TABLE 7

| | Catalyst | | |
|---|---|---|---|
| | MATO-1 | MATO-2 | MATO-3 |
| Reaction temperature (° C.) | 500 | 500 | 500 |
| Conversion rate of methanol (%) | 100 | 100 | 100 |
| Distribution of total products (wt %) | | | |
| $C_1$-$C_5$ | 50.32 | 51.86 | 51.21 |
| $C_6^+$ | 49.68 | 48.14 | 48.79 |
| Total | 100.00 | 100.00 | 100.00 |

* $C_6^+$ represents the hydrocarbon products with carbon number no less than six.

TABLE 8

| | Catalyst | | |
|---|---|---|---|
| | MATO-1 | MATO-2 | MATO-3 |
| Reaction temperature (° C.) | 500 | 500 | 500 |
| Conversion rate of methanol (%) | 100 | 100 | 100 |
| Distribution of $C_1$-$C_5$ products (wt %) | | | |
| $CH_4$ | 1.22 | 1.23 | 1.21 |
| $C_2H_4$ | 52.42 | 52.23 | 52.11 |
| $C_2H_6$ | 0.06 | 0.06 | 0.06 |
| $C_3H_6$ | 38.53 | 38.99 | 39.34 |
| $C_3H_8$ | 0.39 | 0.26 | 0.26 |
| $C_4$ | 5.88 | 5.86 | 5.78 |
| $C_5$ | 1.50 | 1.38 | 1.25 |
| Total | 100.00 | 100.00 | 100.00 |
| $C_2H_4 + C_3H_6$ | 90.95 | 91.22 | 91.45 |

TABLE 9

| | Catalyst | | |
|---|---|---|---|
| | MATO-1 | MATO-2 | MATO-3 |
| Reaction temperature (° C.) | 500 | 500 | 500 |
| Conversion rate of methanol (%) | 100 | 100 | 100 |
| Distribution of *$C_6^+$ products (wt %) | | | |
| Benzene | 4.89 | 5.05 | 4.96 |
| Toluene | 14.32 | 14.54 | 14.37 |

TABLE 9-continued

| | Catalyst | | |
|---|---|---|---|
| | MATO-1 | MATO-2 | MATO-3 |
| Ethyl benzene | 1.13 | 1.15 | 1.12 |
| Xylene | 56.20 | 56.76 | 56.23 |
| Trimethyl benzene | 14.19 | 13.17 | 13.92 |
| Tetramethylbenzene | 5.76 | 5.61 | 5.89 |
| Others | 3.51 | 3.72 | 3.51 |
| Total | 100 | 100 | 100 |

*$C_6^+$ represents the hydrocarbon products with carbon number no less than six.

Example 6: Evaluation for Reactions

The MATO-1, MATO-2 and MATO-3 catalysts were used as the catalysts in the reactions. The catalysts were tabletted, crushed and then sieved to 40-60 meshes. Ten grams of each catalyst was loaded into a reactor, and treated in air at 550° C. for 1 hour followed by a cooling process in nitrogen to reach the reaction temperature of 500° C. Arene solutions were prepared according to the requirement for the proportions of benzene, toluene, xylene, trimethyl benzene and tetramethylbenzene in the $C_6^+$ products obtained from the methanol conversion performed on MATO-2 catalyst, as shown in Table 6 of Example 4. The prepared arene solutions and methanol (calculated by $CH_2$), in a ratio of 0.5:1 by weight, were pumped into the reactors by a metering pump, then they were contacted and reacted with the catalysts. Dimethyl ether was fed in a weight space hourly velocity of 3 $h^{-1}$. The pressure in the reaction system was adjusted to 1.0 MPa using a back pressure valve. The reaction products were analyzed online by gas chromatography. The compositions of the total products, the $C_1$-$C_5$ component and the $C_6^+$ component are shown in Tables 10, 11 and 12. In the total products, the $C_1$-$C_5$ component accounted for 67.46 wt %, 68.57 wt % and 68.83 wt %, respectively; whereas the $C_6^+$ component accounted for 32.54 wt %, 31.43 wt % and 31.17 wt %, respectively. In the $C_1$-$C_5$ components, the selectivity for ethylene and propylene was 90.76 wt %, 91.03 wt % and 90.90 wt %, respectively.

TABLE 10

| | Catalyst | | |
|---|---|---|---|
| | MATO-1 | MATO-2 | MATO-3 |
| Reaction temperature (° C.) | 500 | 500 | 500 |
| Conversion rate of methanol (%) | 100 | 100 | 100 |
| Distribution of total products (wt %) | | | |
| $C_1$-$C_5$ | 67.46 | 68.57 | 68.83 |
| $C_6^+$ | 32.54 | 31.43 | 31.17 |
| Total | 100.00 | 100.00 | 100.00 |

* $C_6^+$ represents the hydrocarbon products with carbon number no less than six.

TABLE 11

| | Catalyst | | |
|---|---|---|---|
| | MATO-1 | MATO-2 | MATO-3 |
| Reaction temperature (° C.) | 500 | 500 | 500 |
| Reaction pressure (MPa) | 1.0 | 1.0 | 1.0 |
| Conversion rate of dimethyl ether (%) | 100 | 100 | 100 |

TABLE 11-continued

| | Catalyst | | |
|---|---|---|---|
| | MATO-1 | MATO-2 | MATO-3 |
| Distribution of $C_1$-$C_5$ products (wt %) | | | |
| $CH_4$ | 1.42 | 1.48 | 1.59 |
| $C_2H_4$ | 54.35 | 55.21 | 54.98 |
| $C_2H_6$ | 0.13 | 0.09 | 0.21 |
| $C_3H_6$ | 36.41 | 35.82 | 35.92 |
| $C_3H_8$ | 0.83 | 0.65 | 0.83 |
| $C_4$ | 5.55 | 5.51 | 5.33 |
| $C_5$ | 1.31 | 1.25 | 1.14 |
| Total | 100.00 | 100.00 | 100.00 |
| $C_2H_4 + C_3H_6$ | 90.76 | 91.03 | 90.90 |

TABLE 12

| | Catalyst | | |
|---|---|---|---|
| | MATO-1 | MATO-2 | MATO-3 |
| Reaction temperature (° C.) | 500 | 500 | 500 |
| Reaction pressure (MPa) | 1.0 | 1.0 | 1.0 |
| Conversion rate of dimethyl ether (%) | 100 | 100 | 100 |
| Distribution of *$C_6^+$ products (wt %) | | | |
| Benzene | 4.45 | 4.76 | 4.87 |
| Toluene | 13.96 | 14.21 | 13.58 |
| Ethyl benzene | 1.17 | 1.28 | 1.22 |
| Xylene | 56.43 | 56.41 | 56.73 |
| Trimethyl benzene | 13.97 | 13.61 | 13.93 |
| Tetramethylbenzene | 5.76 | 6.32 | 5.81 |
| Others | 3.43 | 3.41 | 3.86 |
| Total | 100 | 100 | 100 |

*$C_6^+$ represents the hydrocarbon products with carbon number no less than six.

The invention claimed is:

1. A process for producing ethylene and propylene from methanol and/or dimethyl ether, comprising the steps of;
   (a) contacting methanol and/or dimethyl ether with a catalyst to generate a first stream containing hydrocarbons, the catalyst produced by the steps consisting of:
      (i) impregnating a HZSM-5 and/or a HZSM-11 zeolite molecular sieve in a lanthanum nitrate solution for 1-12 hours, followed by filtering, drying and calcining to obtain a lanthanum-modified molecular sieve;
      (ii) impregnating said obtained lanthanum-modified molecular sieve in one or more silicon sources selected from the group consisting of tetramethyl silicate, tetraethyl silicate, and silicon tetraethyl for 1-12 hours, followed by filtering, drying and calcining to obtain a molecular sieve catalyst co-modified by lanthanum and silanization;
   (b) separating said first stream obtained from step (a) into a first $C_1$-$C_5$ component and a first $C_{6+}$ component;
   (c) mixing said first $C_{6+}$ component obtained from step (b) with methanol and/or dimethyl ether to generate a mixture material, and contacting the mixture material with said catalyst to generate a second stream containing hydrocarbons;
   (d) separating said second stream obtained from step (c) into a second $C_1$-$C_5$ component and a second $C_{6+}$ component, wherein said second $C_1$-$C_5$ component contains ethylene and propylene and is collected as a target product and said second $C_{6+}$ component is recycled to step (c); and
   (e) repeating step (c) and step (d), wherein the mixture material formed by mixing said second $C_{6+}$ component obtained in step (d) with methanol and/or dimethyl ether is used in step (c), so that said second $C_1$-$C_5$ component containing ethylene and propylene is obtained continuously;
   wherein said catalyst co-modified by lanthanum and silanization is the only catalyst used in the process, said catalyst is loaded by lanthanum, and a surface acidity of said catalyst is modified by silicon compounds; and
   wherein a loading amount of said lanthanum is 0.5-5 wt % of a total weight of said catalyst, and a loading amount of said silicon compounds, which is based on silicon oxide, is 0.1-10 wt % of the total weight of said catalyst.

2. The process according to claim 1, wherein process is carried out at a temperature of 400-600° C. and a pressure of 0-2.0 MPa, and methanol and/or dimethyl ether are fed at a weight hourly space velocity of 0.2-10 $h^{-1}$.

3. The process according to claim 1, wherein the process is conducted in a fixed bed, a moving bed or a fluidized bed reactor.

4. The process according to claim 1, wherein the loading amount of said lanthanum is 1-5 wt % of the total weight of said catalyst; and the loading amount of said silicon compounds, which is based on silicon oxide, is 1-10 wt % of the total weight of said catalyst.

5. The process according to claim 1, wherein said silicon source is tetraethyl silicate.

6. A process for producing ethylene and propylene from methanol and/or dimethyl ether, comprising the steps of;
   (a) contacting methanol and/or dimethyl ether with a catalyst to generate a first stream containing hydrocarbons, the catalyst produced by the steps consisting of:
      (i) impregnating a HZSM-5 and/or a HZSM-11 zeolite molecular sieve in a lanthanum nitrate solution for 1-12 hours, followed by filtering, drying and calcining to obtain a lanthanum-modified molecular sieve;
      (ii) impregnating said obtained lanthanum-modified molecular sieve in one or more silicon sources selected from the group consisting of tetramethyl silicate, tetraethyl silicate, and silicon tetraethyl for 1-12 hours, followed by filtering, drying and calcining to obtain a molecular sieve catalyst co-modified by lanthanum and silanization;
   (b) separating said first stream obtained from step (a) into a first $C_1$-$C_5$ component and a first $C_{6+}$ component;
   (c) mixing said first $C_{6+}$ component obtained from step (b) with methanol and/or dimethyl ether to generate a mixture material, and contacting the mixture material with said catalyst to generate a second stream containing hydrocarbons;
   (d) separating said second stream obtained from step (c) into a second $C_1$-$C_5$ component and a second $C_{6+}$ component, wherein said second $C_1$-$C_5$ component contains ethylene and propylene and is collected as a target product and said second $C_{6+}$ component is recycled to step (c); and
   (e) repeating step (c) and step (d), wherein the mixture material formed by mixing said second $C_{6+}$ component obtained in step (d) with methanol and/or dimethyl ether is used in step (c), so that said second $C_1$-$C_5$ component containing ethylene and propylene is obtained continuously;

wherein said catalyst co-modified by lanthanum and silanization is loaded by lanthanum, and a surface acidity of said catalyst is modified by silicon compounds; and wherein a loading amount of said lanthanum is 0.5-5 wt % of a total weight of said catalyst, and a loading amount of said silicon compounds, which is based on silicon oxide, is 0.1-10 wt % of the total weight of said catalyst.

* * * * *